United States Patent [19]

Walworth

[11] 4,009,277
[45] Feb. 22, 1977

[54] 1,2-DIALKYL-3,4,5-TRISUBSTITUTED PYRAZOLIUM SALTS AS FUNGICIDAL AGENTS

[75] Inventor: Bryant Leonidas Walworth, Pennington, N.J.

[73] Assignee: American Cyanamid Company, Stamford, Conn.

[22] Filed: July 23, 1975

[21] Appl. No.: 598,527

Related U.S. Application Data

[63] Continuation-in-part of Ser. No. 541,900, Jan. 17, 1975, abandoned.

[52] U.S. Cl. .............................................. 424/273
[51] Int. Cl.² .......................................... A01N 9/22
[58] Field of Search .................................... 424/273

[56] References Cited

UNITED STATES PATENTS 2,721,143  10/1955  Kraft et al. ........................ 424/273

OTHER PUBLICATIONS

Chemical Abstracts, vol. 79 (1973), p. 92210a.

*Primary Examiner*—V. D. Turner
*Attorney, Agent, or Firm*—Harry H. Kline

[57]          ABSTRACT

There is provided a method for controlling fungi either by contacting the same with a 1,2-dialkyl-3,4,5-trisubstituted pyrazolium salt or by applying said pyrazolium salt to the foliage of a plant susceptible to attack by fungi.

18 Claims, No Drawings

1,2-DIALKYL-3,4,5-TRISUBSTITUTED PYRAZOLIUM SALTS AS FUNGICIDAL AGENTS

This application is a continuation-in-part of my co-pending application, Ser. No. 541,900, filed on Jan. 17, 1975, now abandoned.

As is known, 1,2-dialkyl-3,5-diphenylpyrazolium salts and their use as herbicidal agents, particularly as herbicidal agents effective for the selective control of wild oats (Avena spp.) - in the presence of certain small grains, are disclosed in Klingsberg et al. Netherlands Application No. 7,217,015, published on June 19, 1973; Derwent publication No. 380549-C.

Although the 1,2-dialkyl-3,5-diphenylpyrazolium salts in the above-mentioned reference are uniquely effective for the selective control of wild oats, the compounds are not disclosed as fungicidal agents. Nor are said compounds indicated to be useful for protecting living plants from attack by fungal organisms.

Moreover, in co-pending U.S. Application Ser. No. 487,826, filed on July 12, 1974, it is disclosed that the substitution in the 4-position of the pyrazolium ring in lieu of hydrogen, particularly by alkoxy, markedly alters the spectrum of postemergence herbicidal activity of the desired pyrazolium compounds. Such alteration changes the biological activity of the latter compounds by providing them with a much broader spectrum of broadleaf weed and of grass control. Again, no mention is made of fungicidal control obtained with 4-substituted pyrazolium compounds.

Surprisingly, it has been found that certain 4-substituted pyrazolium salts are fungicidal and are highly effective for protecting living plants from attack by fungal organism.

The present invention relates to a method for controlling fungi with a small but effective amount of a 1,2dialkyl-3,4,5-trisubstituted pyrazolium salt represented by the structure:

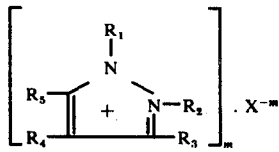

wherein $R_1$ and $R_2$ each represent $C_1$-$C_3$ alkyl and benzyl; $R_3$ and $R_5$ each represent phenyl, halophenyl and tolyl; $R_4$ represents a member selected from the group consisting of $C_1$-$C_{16}$ alkoxy, $C_3$-$C_4$ alkoxy, $C_3$-$C_4$ alkenyloxy, $C_3$-$C_4$ alkynyloxy, $C_3$-$C_4$ haloalkenyloxy, Illustrative of the anions which are suitable for use in the present invention are halides, such as chloride, bromide and iodide; triodide; tribromide; hydroxide; acetate; carbonate; bisulfate; methyl sulfate; benzene sulfonate; perchlorate; $C_1$-$C_4$ alkoxy benzene sulfonate, $C_1$-$C_4$ alkyl benzene sulfonate, preferably p-toluene sulfonate; hydrogen phosphate; and $C_1$-$C_4$ alkane sulfonate.

The preferred compounds utilized herein have the above structure wherein $R_1$ represents methyl, ethyl or benzyl; $R_2$ represents methyl or propyl; $R_3$ represents phenyl, m-chlorophenyl and p-tolyl; $R_5$ represents phenyl, m-chlorophenyl, p-chlorophenyl, m-tolyl and p-tolyl; $R_4$ represents a member selected from the group consisting of methoxy, ethoxy, n and i-propoxy, n-, i- and sec-butoxy, n-pentyloxy, n-hexyloxy, n-heptyloxy, n-octyloxy, n-decyloxy, n- tridecyloxy, N-hexadecyloxy, allyloxy, 2-propynyloxy, 2-chloroallyloxy, 3-chloroallyloxy, benzyloxy, α-methylbenzyloxy, o-(m & p)-chlorobenzyloxy, p-bromobenzyloxy, m-cyanobenzyloxy, p-methylbenzyloxy, p-methoxybenzyloxy, p-nitrobenzyloxy,

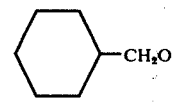

and 2,4-dinitrophenoxy; x represents an anion selected from the group consisting of bromide, chloride, iodide, methyl sulfate, boron tetrafluoride and perchlorate.

A more preferred group of compounds have the above structure wherein $R_1$ represents methyl and ethyl; $R_2$ is methyl; $R_3$ represents phenyl and m-chlorophenyl; $R_5$ represents phenyl, m-chlorophenyl and m-tolyl; $R_4$ represents a member selected from the group consisting of methoxy, ethoxy, n- and i-propoxy, n-, i- and sec-butoxy, n-pentyloxy, n-hexyloxy, n-heptyloxy, n-octyloxy, n-decyloxy, n-tridecyloxy, n-hexadecyloxy, allyloxy, 3-chloroallyloxy, 2-propynyloxy, benzyloxy, α-methylbenzyloxy, o-, m- and p-chlorobenzyloxy, p-bromobenzyloxy, m-trifluoromethyl benzyloxy, p-methylbenzyloxy, or p-methoxybenzyloxy, x represents an anion selected from the group consisting of bromide, chloride, iodide, methyl sulfate and perchlorate.

In general, the pyrazolium compounds having the structure (I):

(I)

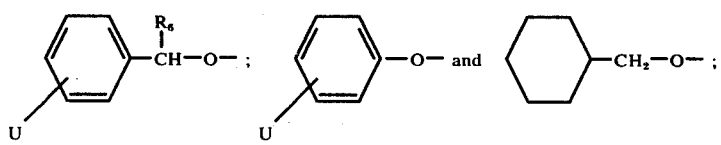

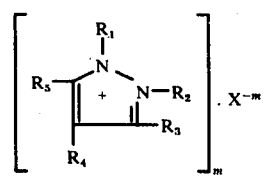

$R_6$ represents hydrogen and methyl; U represents a member selected from the group consisting of hydrogen, methyl, methoxy, bromine, chlorine, cyano, trifluoromethyl, nitro and 2,4-dinitro; X represents an anion with a charge of from 1 to 3 and, preferably, 1 to 2; $m$ represents an integer from 1 to 3.

wherein $R_1$, $R_2$, $R_3$, $R_4$, $R_5$, X and $m$ are as defined above, can be prepared by alkylation of a formula (II) pyrazole or alkylation of an alkali metal salt of a pyrazolium hydroxide (III). These reactions may be graphically illustrated as Method A or as Method B as follows:

Method A

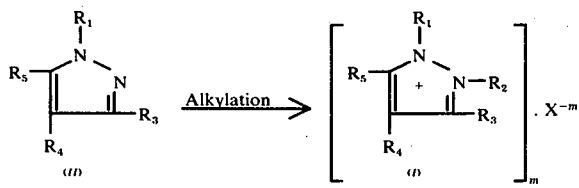

or

Method B

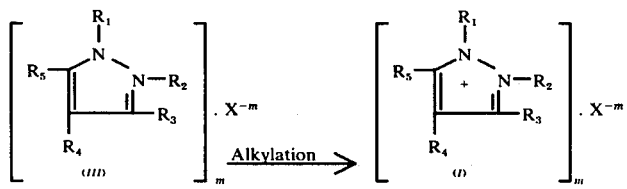

wherein $R_1$, $R_2$, $R_3$, $R_4$, $R_5$, $m$ and X are as defined above.

In accordance with the procedure of Method A, a pyrazole, such as depicted by Formula (II), can be alkylated in toluene, xylene or similar solvent, with one or more equivalents of an alkylating agent, such as dimethylsulfate, methyliodide, methylbromide or p-methyl-toluenesulfonate. This reaction is generally carried out at a temperature between 70° C. and 150° C. and preferably, at a temperature between 70° C. and 130° C.

Illustrative alkylating agents include alkyl halides, alkyl sulfates, dialkyl sulfates, alkyl phosphates, alkyl hydrogen sulfates, and alkyl toluene sulfonates. Among the preferred alkylating reagents are the alkyl halides, such as methyl, ethyl, n-propyl, and benzylchloride or the corresponding iodides; alkyl sulfates dialkyl sulfates, alkyl hydrogen sulfates, and toluene sulfonates.

In carrying out the alkylation reaction, it may be expedient to initially form a salt having an anion other than that which it is desired to employ in the fungicidal processes of the present invention. In such cases, the exchange in anion may be conveniently made in a subsequent step. The exchange can be effected by treating the initially formed salt with an ion exchange resin. Among the suitable ion exchange resins, one can mention a strong base organic anion exchanger, such as Dowex 1-X8, which is a quaternary alkylammonium resin. Where the resin is supplied as the salt of an anion other than that desired, it is pretreated with an aqueous solution of a salt of the desired anion. For example, if the resin is supplied as a quaternary ammonium chloride and it is desired to produce a pyrazolium nitrate, one would pretreat the resin with an aqueous solution of sodium nitrate.

Exchange of the anion X, in the formula (I) pyrazolium salt, can also be achieved directly by exchange with an appropriate acid, e.g., the methyl sulfate can be exchanged for the bromide, iodide or perchlorate anion, by treatment thereof with aqueous hydrobromic acid, aqueous hydroiodic acid or aqueous perchloric acid, respectively. In addition, the methyl sulfate can be exchanged for other anions, such as $Cl^-$, $NO_3^-$, or $CH_3COO^-$, by adding to an aqueous solution of the methyl sulfate salt, such salts as calcium chloride, calcium nitrate or calcium acetate either as a salt or as an aqueous solution. Insoluble calcium methyl sulfate precipitates and is removed by filtration. The desired pyrazolium salt can be isolated as a solid from the aqueous medium by extraction with chloroform and then removal of the chloroform by evaporation. The bromides or iodides can also be conveniently converted to the tribromides or triodides by the addition of bromide or iodine to a solution of the monobromide or monoiodide in a solvent, such as ethanol.

An alternative method for the preparation of the formula (I) pyrazolium salts, wherein $R_4$ is $C_3$-$C_4$ alkenyloxy, $C_1$-$C_{16}$ alkoxy, or

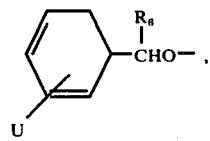

wherein $R_6$ and U are as defined above, identified as Method B, involves the alkylation of an alkali metal salt of a formula (III) pyrazolium hydroxide. It is generally carried out in the presence of an aprotic solvent, such as dimethylformamide (DMF), dimethylsulfoxide (DMSO), xylene, toluene, benzene, or the like, at a temperature between about 25° C. and 100° C. In practice, the 4-hydroxy-1,2-dialkyl-3,5-disubstituted pyrazolium salt is initially treated with an alkali metal (i.e., sodium or potassium) hydroxide or an alkali metal $C_1$-$C_4$ alkoxide such as sodium or potassium methoxide or ethoxide, in the presence of an aprotic solvent at an elevated temperature, eg., from 50° C. to 80° C., then cooled and, thereafter, treated with an alkylating agent as described above.

Advantageously, the pyrazolium salts generally demonstrate a high degree of water solubility and lend themselves to the preparation of aqueous concentrates. Among the preferred salts are the methyl sulfates, hydrogen sulfates, chlorides and bromides. In practice, the aqueous concentrates may be applied directly as a liquid spray to the foliage of plants or they may be further diluted with water and applied as dilute aqueous sprays to said plants.

It has been found that the compounds of this invention are useful for the control of fungi which infect many living plants. They are particularly effective for controlling powdery mildew, especially on grains such as barley and wheat, on vines such as cucumbers, grapes and pumpkin and on fruit and nut trees such as apples, pears and pecans. However, they are also effective for controlling fungi which are the causative agents for rice blast, late blight and apple scab.

In utilizing the above-identified pyrazolium salts for protecting plants from pathogenic fungi, it has been found most advantageous to apply the active material to the foliage of the plant in the form of a liquid, preferably, aqueous spray. Solutions or suspension containing from about 20 ppm to 5600 ppm and, preferably, from 50 to 500 ppm, of the pyrazolium cation are generally highly effective for this use.

As the pyrazolium salts disclosed herein exhibit substantial water solubility, such salts can simply be dissolved in water and applied directly, or a surfactant or mixture of surfactants can be added to an aqueous mixture thereof.

The pyrazolium salts can also be prepared as wettable powders or as water miscible concentrates which are diluted with water or other suitable polar solvent, generally at the site of use, and then applied as a dilute aqueous spray. Generally, such sprays are applied at the volume rate of from about 938 l/ha to 1877 l/ha or about 100 to 200 gal per acre. It is, of course, obvious that smaller or larger volumes of liquid spray may be employed. For instance, from 400 to 4000 l/ha can be used depending on a plurality of factors such as type of crop, the plant spacing and the amount of foliage per plant being treated.

While fungicides treatments are generally discussed in terms of concentration of active ingredient in ppm in the solution or suspension, it should also be noted that, with the compounds of the present invention, it is generally desirable to apply the pyrazolium salt in an amount sufficient to provide from about 0.56 to 11.8 kg/ha and, preferably, from 0.56 to 4.48 kg/ha of the pyrazolium cation.

Wettable powder formulations can be prepared by grinding together about 25% to 95% by weight of the pyrazolium salt and about 75% to 5% by weight of a solid diluent such as attapulgite, kaolin, bentonite, diatomaceous earth, silica, talc fullers earth or the like. To this mixture is added about 1% to 5% by weight of a dispersing agent such as the calcium salt of a polymerized alkyl aryl sulfonic acid, sodium lignosulfonate, or sodium salt of condensed naphthalene sulfonic acid and about 1% to 5% by weight of a surfactant, such as polyoxyethylated vegetable oil, alkyl phenoxy polyoxyethylene ethanol, sodium alkyl naphthalene sulfonate is also blended with the formulation.

The water-miscible concentrates are prepared by dissolving from 15% to 70% by weight of the compound in 85% to 30% by weight of a water-miscible solvent, such as water itself or another polar water-miscible solvent, such as 2-methoxy ethanol, methanol, propylene glycol, diethylene glcyol, diethylene glycol monoethyl ether, formamide, and methylformamide. Application of the material is made by adding a predetermined quantity of the watermiscible concentrate to a spray tank and applying as such or in combination with additional suitable diluent, such as a further quantity of water or one of the above polar solvents mentioned above.

The performance of the product in the above formulations, which are applied as liquid sprays, is improved by adding a surfactant or blend of surfactants thereto. Conventional nonionic surfactants are preferred and the surfactants are, preferably, added to the spray tank at the rate of 0.1% to 5% by volume to provide good wetting of the spray solution on plant foliage.

Suitable nonionic surfactants include alkyl polyoxyethylene ethers, polyoxyethylene (20) sorbitan monolaurate, polyoxyethylene (20) sorbitan monooleate, alkylarylpolyglycol ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxy propylenes, aliphatic polyethers, aliphatic polyesters, alkylaryl polyoxyethylene glycols, and the like. Especially preferred are nonionic surfactants having a hydrophilic-lipophilic balance (HLB) of from 11 to 16. This conventional surfactant classification test is described, for instance, at pages 232 et seq. of *Emulsion Theory and Practice* by Paul Becker, Rheinholt Publishing Corporation, second edition (1965); also available as No. 162 in the American Chemical Society's Monograph Series.

Preferred methods employ water as the solvent and a hereinabove described 4-alkoxypyrazolium salt as the active ingredient.

The invention is further illustrated by the examples set forth below which are provided by way of illustration and not by way of limitation.

EXAMPLE 1

To determine the effectiveness of pyrazolium salts as fungicidal agents a variety of pathogenic fungi, host plants and pyrazolium salts are used in the following tests. Pathogens host plants, the method testing and the rating system used are reported below along with the data obtained. *Pathogens:* Piricularia oryzae Carvara, the rice blast pathogen. *Phytophthora infestans* (Mont) Dby., the late blight fungus of tomatoes and potatoes. *Venturia inaequalis* (Cke.) Wint. which causes apple scab. *Erysiphe cichoracearum* DC, the cause of powdery mildew on cucurbits. *Podosphaera Leucotricha* (E. and E.) Salm., the cause of powdery mildew of apples and pears. *Erysiphe graminis* f. sp. *tritici* the cause of powdery mildew on wheat. *Erysiphe graminis* f. sp. *hordei* the cause of powdery mildew on barley. *Host Plants:* Rice (*Oryza sativa*) (Cv. Nato) Tomato (Dycopersicum esculentum) (Cv. Bonny best) Cucumber (*Cucumis sativus*) (Cv. Marketer) Apple (*Malus Sylvestris*) (Seedling) Wheat (*Triticum aestivum*) (Cv. Bonanza) Barley (Hordeum Vulgare) (Cv. Larker)

Plants are individually grown in 5.08 cm peat squares and assembled in 7.62 cm × 25.4 cm pressed fibre flats the week prior to spraying. With the exception of rice and wheat, a single specimen of each species is used. A separate flat is used for those plants in the mildew evaluation. The complete test system is shown below:

| Series No. 1 | Series No. 2 |
| --- | --- |
| Rice: rice blast | Apple: powdery mildew |
| Apple: apple scab | Cucumber: powdery mildew |
| Tomato: late blight | Wheat: powdery mildew |
| | Barley: powdery mildew |

Spray solutions are prepared at a final concentration of 50, 100 or 500 ppm in 50 ml of 50% aqueous acetone. In all cases, acetone is added first to solubilize the compound and solutions made to final volume with deionized water.

Two flats, with plants for each treatment, one each from Series 1 and 2 above, are sprayed simultaneously on a turntable with 50 ml of the test solution. Spray is provided by two fixed Spraying System Co. nozzles mounted to deliver vertical and hortizontal solid cone spray patterns. Immediately thereafter, all plants, are returned to the greenhouse to permit the deposit to dry.

After the plants have dried, Series 1 and 2 are separately inoculated. Plants in Series 1 are inoculated with conidial suspensions of the respective pathogens using a DeVilbiss paint sprayer operated at 4-6 psig and immediately transferred to a controlled temperature/humidity cabinet (ambient temperature RH~95%). Plants in Series 2 are dusted with respective powdery mildew conidia and then removed to a plant culture room (10 hr. light, 70°–74° F, 45% RH), to await disease development. Plants in Series 1 are held 4 days in the cabinet then transferred to the greenhouse to await disease expression.

Performance Rating

All plants are rated for disease severity on a scale of 1-7 (clean-kill), as described below:

| Rating | Description |
| --- | --- |
| 1 | Nil |
| 2 | Trace disease |
| 3 | Slight disease |
| 4 | Moderate disease |
| 5 | Heavy disease |
| 6 | Severe disease |
| 7 | Kill |

Data obtained are reported in Tables I and II below. Ratings reflect only levels where effective control was observed and are mean ratings for all tests carried out with any given compound.

Table I

| Disease Severity of Plants Sprayed to Run-off with Indicated Rates (ppm) | | | | | | | | | |
| --- | --- | --- | --- | --- | --- | --- | --- | --- | --- |
| Compound | Rice Blast | | | Apple Scab | | | | | |
| | 500 | 100 | 50 | 500 | 100 | 50 | | | |
| Acceptable Control | | 1-4 | | | 1-4 | | | | |
| Untreated Controls | | 5.6 | | | 5.7 | | | | |
| 4-Methoxy-1,2-dimethyl-3,5-diphenylpyrazolium perchlorate | 4.0 | 4.0 | 3.0 | 4.0 | | | | | |
| 4-Ethoxy-1,2-dimethyl-3,5-diphenylpyrazolium perchlorate | | | | 4.0 | | | | | |
| 1,2-Dimethyl-3,5-diphenyl-4-propoxypyrazolium bromide | | | | 2.0 | | | | | |
| 1,2-Dimethyl-3,5-diphenyl-4-propoxypyrazolium iodide | | | | 1.0 | | | | | |
| 4-Isopropoxy-1,2-dimethyl-3,5-diphenylpyrazolium methyl sulfate | | | | 3.0" | | | | | |
| 1,2-Dimethyl-3,5-diphenyl-4-(2-propynyloxy)-pyrazolium perchlorate | | | | 3.0 | | | | | |
| Compounds Acceptable control Untreated Controls | Rice Blast | | | Tom date blight | | | Apple Scale | | |
| | 500 | 100 | 50 | 500 | 100 | 50 | 500 | 100 | 50 |
| 1.2-dimethyl-3,5-diphenyl-4-methoxypyrazolium methyl sulfate | | | | | | | 4 | | |
| 1,2-dimethyl-3-phenyl-4-n-propoxy-5-m-tolylpyrazolium methyl sulfate | | | | | | | 3 | | |
| 4-n-decyloxy-1,2-dimethyl-3,5-diphenylpyrazolium methyl sulfate - H₂O | 4.0 | | | | | | | | |
| 5-p-chlorophenyl-1,2-dimethyl-3-phenyl-4-n-propoxypyrazolium methyl sulfate | | | | | | | 4 | | |
| 3,5-di-m-chlorophenyl-1,2-dimethyl-4-n-propoxypyrazolium methyl sulfate | | | | | | | 4 | | |
| 1,2-dimethyl-3,5-di-p-tolyl-4-n-propoxypyrazolium boron tetrafluoride | | | | | | | 4 | | |
| 4-(2-chloroallyloxy)-1,2-dimethyl-3,5-diphenylpyrazolium methyl sulfate | | | | | | | 4 | 3 | |
| 4-(3-chloroallyloxy)-1,2-dimethyl-3,5-diphenylpyrazolium methyl sulfate | | 4 | | | 5 | | | 4 | |
| 4-sec-butoxy-1,2-dimethyl-3,5-diphenylpyrazolium methyl sulfate | | | | | | | 4 | 4 | |
| 1,2-dimethyl-3,5-diphenyl-4-n-pentyloxypyrazolium methyl sulfate - H₂O | | | | | | | | | 4 |
| 1,2-dimethyl-3,5-diphenyl-4-n-octyloxypyrazolium methyl sulfate | | | | | | | | | 4 |
| 1,2-dimethyl-3,5-diphenyl-4-n-tridecyloxypyrazolium methyl sulfate | | | | | | | 2 | | |
| 1,2-dimethyl-3,5-diphenyl-4-n-hexadecyloxypyrazolium methyl sulfate | | | | | | | 4 | | |
| 4-benzyloxy-1,2-dimethyl-3,5-diphenylpyrazolium methyl sulfate | | | | | | | 4.0 | 4.3 | |
| 4-(2-chlorobenzyloxy)-1,2-dimethyl-3,5-dephenylpyrazolium methyl sulfate | | | | 4 | 4 | | 4 | 4 | |
| 4-(3-chlorobenzyloxy)-1,2-dimethyl-3,5-diphenylpyrazolium methyl sulfate | | | | | 4 | | 4.5 | | |
| 1,2-dimethyl-3,5-diphenyl-4-[(3-trifluoromethyl)benzyloxy]-pyrazolium methyl sulfate | | | | | | 5 | | | |
| 4-[(3-cyano)benzyloxy]-1,2-dimethyl-3,5-diphenylpyrazolium methyl sulfate | 4 | | | 5 | | | | | |
| 4-(4-bromobenzyloxy)-1,2-dimethyl-3,5-diphenylpyrazolium methyl sulfate | | | | 5 | | 5 | 4.0 | | |

Table I-continued

| Compound | 500 | 100 | 50 |
|---|---|---|---|
| 4-(4-chlorobenzyloxy)-1,2-dimethyl-3,5-diphenylpyrazolium methyl sulfate | | 5 | 4 |
| 1,2-dimethyl-3,5-diphenyl-4-(4-methylbenzyloxy)pyrazolium methyl sulfate | | 5 | |
| 1,2-dimethyl-3,5-diphenyl-4-[(4-methoxy)benxyloxy]pyrazolium methyl sulfate | | 5 | |
| 1,2-dimethyl-3,5-diphenyl-4-(4-nitrobenzyloxy)pyrazolium methyl sulfate | | 5 | 5 | 4 |
| 1,2-dimethyl-3,5-diphenyl-4-(α-methyl-benzyloxy)pyrazolium methyl sulfate | 4 | | 4 |
| 4-cyclohexylmethoxy-1,2-dimethyl-3,5-diphenylpyrazolium methyl sulfate | | | 4 |
| 1,2-dimethyl-4-[(2,4-dinitro)phenoxyl]-3,5-diphenyl pyrazolium methyl sulfate | | 3 | |

Table II

| | Disease Severity of Plants Sprayed to Run-off with Indicated Rates (ppm) | | | | | | | | | | | |
|---|---|---|---|---|---|---|---|---|---|---|---|---|
| Compound | CUC Powdery | | | Wheat Powdery | | | Apple Powdery | | | Barley Powdery | | |
| | 500 | 100 | 50 | 500 | 100 | 50 | 500 | 100 | 50 | 500 | 100 | 50 |
| Acceptable Rating | | 1-4 | | | 1-3 | | | 1-3 | | | 1-4 | |
| Untreated Control | | 6.0 | | | 6.0 | | | 5.1 | | | 6.0 | |
| 4-Methoxy-1,2-dimethyl-3,5-diphenylpyrazolium perchlorate | | 4.0 | | 1.0 | 1.0 | 1.0 | | | | | | |
| 4-Methoxy-1,2-dimethyl-3,5-diphenylpyrazolium iodide | 3.0″ | | | 1.3 | 3.0 | | | | | 1.0 | 3.0 | 2.0 |
| 4-Methoxy-1,2-dimethyl-3,5-diphenylpyrazolium bromide | | | | 1.0″ | | | | | | | | |
| 4-Ethoxy-1,2-dimethyl-3,5-diphenylpyrazolium perchlorate | 3.0″ | | | 2.0 | | | | | | | | |
| 1,2-Dimethyl-3,5-diphenyl-4-propoxypyrazolium perchlorate | 3.7 | | | 1.1 | 1.6 | 1.6 | | | | 1.0 | 1.5 | 2.0 |
| 1,2-Dimethyl-3,5-diphenyl-4-propoxypyrazolium methyl sulfate | | | | 1.0 | 1.0 | 1.0 | 2.0 | 3.0 | 3.0 | 1.0 | 2.0 | 3.0 |
| 1,2-Dimethyl-3,5-diphenyl-4-propoxypyrazolium chloride | 1.0 | | | 1.0 | 1.0 | 1.0 | | | | | | |
| 1,2-Dimethyl-3,5-diphenyl-4-propoxypyrazolium bromide | 1.0 | 3.0 | | 1.0″ | 1.0 | 1.0 | 2.0 | 3.0 | | | | |
| 1,2-Dimethyl-3,5-diphenyl-4-propoxypyrazolium iodide | | | | 2.0″ | | | | | | 2.0 | | |
| 4-Isopropoxy-1,2-dimethyl-3,5-diphenylpyrazolium methyl sulfate | 1.0″ | | | 2.0″ | | | | | | 2.0″ | | |
| 4-Isopropoxy-1,2-dimethyl-3,5-diphenylpyrazolium perchlorate | | | | 2.0″ | | | | | | 2.0″ | | |
| 4-(Allyloxy)-1,2-dimethyl-3,5-diphenylpyrazolium perchlorate | | | | 1.0 | 2.0 | 1.0 | | | | | | |
| 1,2-Dimethyl-3,5-diphenyl-4-(2-propynyloxy)pyrazolium perchlorate | 4.0 | | | 2.0 | 2.0 | | | | | | | |
| 1,2-Dimethyl-3,5-diphenyl-4-(2-propynyloxy)pyrazolium methyl sulfate | 3.0 | | | 1.0 | | | | | | | | |
| 1-Ethyl-4-methoxy-2-methyl-3,5-diphenylpyrazolium perchlorate | | | | 2.0 | | | | | | | | |
| 4-Methoxy-1-methyl-3,5-diphenyl-2-propylpyrazolium perchlorate | | | | 3.0 | | | | | | | | |
| 1-Benzyl-4-methoxy-2-methyl-3,5-diphenylpyrazolium methyl sulfate | | | | | | | 3.0 | | | 4.0 | | |
| 1-Benzyl-4-methoxy-2-methyl-3,5-diphenylpyrazolium perchlorate | | | | | | | | | | 4.0 | | |
| 1,2-dimethyl-3,5-diphenyl-4-methoxypyrazolium methyl sulfate | dead | | | 1.5 | 4 | | | | | | | |
| 5-(4-chlorophenyl)-1,2-dimethyl-4-methoxy-3-phenylpyrazolium methyl sulfate | 3 | | | | | | | | | | | |
| 1,2-dimethyl-3-phenyl-4-n-propoxy-5-m-tolylpyrazolium methyl sulfate | 1 | | | | | | 1 | | | | | |
| 5-(4-chlorophenyl)-1,2-dimethyl-3-phenyl 4-n-propoxypyrazolium methyl sulfate | | | | 4 | | 4 | | | | 4 | | |
| 3,5-di-(3-chlorophenyl)-1,2-dimethyl-4-n-propoxypyrazolium methyl sulfate | 3 | 4 | 1 | 3 | | | | | | 1 | 4 | |
| 1,2-dimethyl-3,5-diphenyl-4-n-propoxypyrazolium methyl sulfate | | | | 2 | | | | | | 2 | | |
| 4-(2-chloroallyloxy)-1,2-dimethyl-3,5-diphenylpyrazolium methyl sulfate | 4 | | | 3 | 3 | | | | | 4 | | |
| 4-(3-chloroallyloxy)-1,2-dimethyl-3,5-diphenylpyrazolium methyl sulfate | | | | 2 | 3 | | 4 | 3 | | 1 | 3 | |
| 4-n-butoxy-1,2-dimethyl-3,5-diphenylpyrazolium perchlorate | 4 | | | 1 | 2 | 2 | | | | 2 | 3 | 4 |
| 4-n-butoxy-1,2-dimethyl-3,5-diphenylpyrazolium methyl sulfate | 1 | 1 | | 1 | 2 | 2 | | | | 2 | 3 | 4 |
| 4-iso-butoxy-1,2-dimethyl-3,5-diphenylpyrazolium methyl sulfate | 3 | | | 2 | 2 | | | | | 2 | 3 | |
| 4-sec-butoxy-1,2-dimethyl-3,5-diphenylpyrazolium methyl sulfate | 1.5 | 4.0 | 3.5 | 1.5 | 2.5 | 4.5 | 4.5 | | | 2.0 | 4.5 | |
| 4-sec-butoxy-1,2-dimethyl-3,5-diphenylpyrazolium perchlorate | | | | 2 | 3 | 4 | | | | 3 | | |
| 1,2-dimethyl-3,5-diphenyl-4-n-pentyloxypyrazolium perchlorate | 4 | | | 1 | 2 | 3 | | | | 1 | 1 | 4 |

Table II-continued

| Compound | Disease Severity of Plants Sprayed to Run-off with Indicated Rates (ppm) | | | | | | | | | | | |
|---|---|---|---|---|---|---|---|---|---|---|---|---|
| | CUC Powdery | | | Wheat Powdery | | | Apple Powdery | | | Barley Powdery | | |
| | 500 | 100 | 50 | 500 | 100 | 50 | 500 | 100 | 50 | 500 | 100 | 50 |
| Acceptable Rating | | 1–4 | | | 1–3 | | | 1–3 | | | 1–4 | |
| Untreated Control | | 6.0 | | | 6.0 | | | 5.1 | | | 6.0 | |
| 1,2-dimethyl-3,5-diphenyl-4-n-pentyloxy-pyrazolium methyl sulfate - ½ H₂O | | 2.5 | 3.5 | 1.0 | 1.5 | 2.5 | 3.0 | | | 1.5 | 3.0 | 3.5 |
| 1,2-dimethyl-3,5-diphenyl-4-n-hexyloxy-pyrazolium methyl sulfate | | 3 | 3 | 2 | 3 | 3 | | | | 2 | 2 | |
| 1,2-dimethyl-3,5-diphenyl-4-n-heptyloxy-pyrazolium methyl sulfate | | 3.0 | 3.5 | 2.0 | 3.0 | 3.5 | 4.5 | | | 1.5 | 2.0 | 4.5 |
| 1,2-dimethyl-3,5-diphenyl-4-n-octyloxy-pyrazolium methyl sulfate | 2 | 2.5 | 3.0 | 2.0 | 2.5 | 3.0 | | | | 1.5 | 3.5 | |
| 4-n-decyloxy-1,2-dimethyl-3,5-diphenyl-pyrazolium methyl sulfate - H₂O | 2 | 3.5 | 3.5 | 1.5 | 3.0 | 3.0 | 3.5 | 4.5 | | 1.5 | 3.0 | 2.5 |
| 1,2-dimethyl-3,5-diphenyl-4-n-tridecyloxy-pyrazolium methyl sulfate | 1 | 3 | 3 | 4 | 2 | 4 | 3 | 4 | 4 | 2 | 1 | 4 |
| 1,2-dimethyl-3,5-diphenyl-4-n-hexadecyloxy-pyrazolium methyl sulfate | | | | 3 | 3 | | | | | 1 | 1.5 | |
| 4-benzyloxy-1,2-dimethyl-3,5-diphenylpyrazolium methyl sulfate | 2.6 | 3.2 | 4.5 | 1.4 | 2.4 | 3.4 | | | | 1.5 | 2.2 | 3.2 |
| 4-(2-chlorobenxyloxy)-1,2-dimethyl-3,5-diphenylpyrazolium methyl sulfate | 2 | 3 | | 3 | | | | | | 4 | | |
| 4-(3-chlorobenzyloxy)-1,2-dimethyl-3,5-diphenylpyrazolium methyl sulfate | 4.0 | 4 | | 2.0 | 3 | | | | | 2.0 | 3 | |
| 1,2-dimethyl-3,5-diphenyl-4-[(3-trifluromethyl)benzyloxy]pyrazolium methyl sulfate | | 4 | 4 | 1 | 3 | 3 | | | | 1 | 3 | 4 |
| 4-(3-cyanobenzyloxy)-1,2-dimethyl-3,5-diphenylpyrazolium methyl sulfate - H₂O | | 4 | | 3 | 4 | 4 | | | | 4 | | |
| 4-(4-bromobenzyloxy)-1,2-dimethyl-3,5-diphenylpyrazolium methyl sulfate | | | | 2.0 | 4 | | | | | 3.0 | 4 | |
| 4-(4-chlorobenzyloxy)-1,2-dimethyl-3,5-diphenylpyrazolium methyl sulfate | 3 | | | 2 | | | | | | 3 | | |
| 1,2-dimethyl-3,5-diphenyl-4(4-methylbenzyloxy)pyrazolium methyl sulfate | 3 | 3 | | 1 | 3 | | | | | 3 | 3 | |
| 1,2-dimethyl-3,5-diphenyl-4-(4-methoxybenzyloxy)pyrazolium methyl sulfate | | | | 2.0 | 4.0 | | | | | 3.0 | 4.5 | 4.0 |
| 1,2-dimethyl-3,5-diphenyl-4-(4-nitrobenzyloxy)pyrazolium methyl sulfate | 4.5 | 4.5 | 4 | 2.5 | 3.0 | 3.5 | | | | 3.5 | 4.0 | 4.5 |
| 1,2-dimethyl-3,5-diphenyl-4-(α-methylbenzyloxy)pyrazolium methyl sulfate | 4 | | | 1 | | | | | | 3 | | |
| 4-cyclohexylmethoxy-1,2-dimethyl-3,5-diphenylpyrazolium methyl sulfate | 2 | 3.5 | 3.0 | 2.5 | 3.0 | 4.5 | | | | 2.0 | 4.5 | |
| 1,2-dimethyl-4-[(2,4-dinitro)phenoxy]-3,5-diphenylpyrazolium methyl sulfate | | | | 4 | | | | | | | | |

EXAMPLE 2

Eradicants for Fungi

In order to determine the effectiveness of the compounds of the present invention as eradicants for fungi, particularly cereal powdery mildew, wheat plants growing in fibre containers, as described in the previous example, are inoculated with conidia of wheat powdery mildew. The plants are then either treated immediately with a solution or suspension of test compound prepared as described in the preceding example, or they are placed in a plant culture room of constant temperature, humidity and day length to undergo an incubation period of 24, 72 or 168 hours. Plants are withdrawn at said intervals and then sprayed with a solution or suspension containing 25, 50 or 100 ppm of test compound. After spraying the plants are replaced in the culture room. Three days after spraying the plants are examined and rated according to the rating system described in the preceding example.

From the data obtained, which are reported in Table III below, it can be seen that the test compounds are highly effective when used as eradicants for powdery mildew.

Table III

Alkoxy 4-Substituted-1,2-dimethyl-3,5-diphenylpyrazolium Salts as Cereal Powdery Mildew Eradicants-Wheat

| Compound | Mean Disease Severity, 2-Replicates Each Treatment (ppm) | | | | | | | | | | | |
|---|---|---|---|---|---|---|---|---|---|---|---|---|
| | 0 Hours Post-inoculation | | | 24 Hours Post-inoculation | | | 72 Hours Post-inoculation | | | 168 Hours Post-inoculation | | |
| | 100 | 50 | 25 | 100 | 50 | 25 | 100 | 50 | 25 | 100 | 50 | 25 |
| 1,2-Dimethyl-3,5-diphenyl-4-propoxy-pyrazolium perchorate | 2.0 | 1.5 | 2.0 | 3.0 | 3.0 | 4.0 | 1.5 | 1.0 | 2.5 | 4.0 | 3.5 | 4.5 |
| 1,2-Dimethyl-3,5-diphenyl-4-propoxy-pyrazolium methyl sulfate | 1.0 | 1.5 | 2.0 | 2.0 | 2.5 | 2.5 | 2.0 | 1.0 | 2.0 | 4.5 | 3.0 | 3.5 |
| Untreated Control | | 4.3 | | | 6.0 | | | 6.0 | | | 6.0 | |

EXAMPLE 3

Preparation of
4-Methoxy-1,2-dimethyl-3,5-diphenylpyrazolium
perchlorate.

Method A

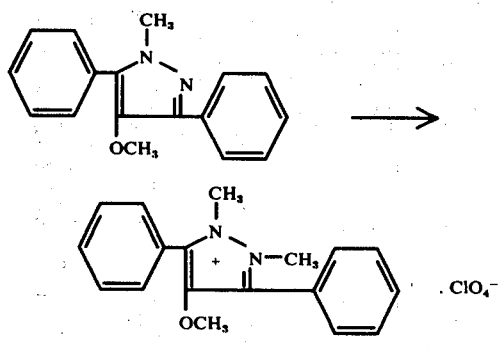

4-Methoxy-1-methyl-3,5-diphenylpyrazole (2.5 g, 0.0095 mole) in molecular sieve-dried toluene (80 ml) is heated to 50° C and dimethyl sulfate (2.5 g, 0.02 mole) is added. The mixture is stirred and heated under reflux for 6 hours, cooled and set aside overnight. Water (100 ml) is then added and this aqueous layer separated and treated with 10% aqueous perchloric acid. After 30 minutes, 0.6 g (16%) of a white powder is filtered off with a melting point of 135°–136° C.

Analysis calculation for $C_{18}H_{19}N_2ClO_5$: C, 57.05; H, 5.06; N, 7.40. Found: C, 56.96; H, 5.17; N, 7.40.

EXAMPLE 4

Preparation of
4-Methoxy-1,2-dimethyl-3,5-diphenylpyrazolium
perchlorate.

Method B

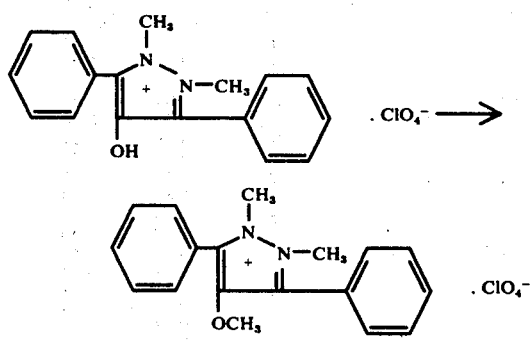

4-Hydroxy-1,2-dimethyl-3,5-diphenylpyrazolium perchlorate (7 g, 0.02 mole) in DMSO (2.5 ml) is added to 5% sodium hydroxide (0.84 g, 0.02 mole) in DMSO (100 ml), dropwise with stirring. The mixture is warmed to 60° C for 5 minutes, then stirred at room temperature for 4 hours. The reaction mixture (75 ml) is treated with methyl iodide (0.43 g, 0.013 mole) and the mixture is stirred at room temperature for 16 hours, then heated at 40° C for 2 hours. On pouring into water, a solid precipitates with melting point 88° C. One crystallization from methanol gives the product with melting point 132°–132.5° C in 53% yield.

EXAMPLE 5

Preparation of
4-Methoxy-1,2-dimethyl-3,5-diphenylpyrazolium
methyl sulfate.

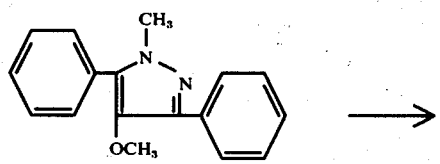

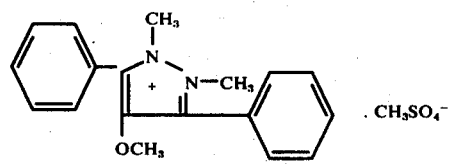

4-Methoxy-1-methyl-3,5-diphenylpyrazole (20 g, 0.076 mole) is suspended in dimethyl sulfate (23 g) at 20° C and the mixture is stirred and the reaction temperature raised to 130° C. At 70° C the mixture becomes a homogeneous solution and at 130° C some darkening occurs. After maintaining the reaction at 130° C for 1 hour, it is cooled and the mixture poured into toluene (250 ml). The toluene layer is decanted off and further toluene is added, decanted off, and this sequence repeated a third time. The residual oil, obtained from the above treatment, is then treated with acetone (10 ml) which has been dried over anhydrous potassium carbonate. This yields a crystalline product which is filtered off and washed with ether. The acetone filtrate is evaporated to give 27.5 g of oil, dissolved in water, and extracted with chloroform. The chloroform layer is evaporated to a small volume and then ether added. A white precipitate is obtained; combined yield 22 g (74%) of melting point 104.5°–105° C is obtained.

EXAMPLE 6

Compounds of the present invention are prepared in accordance with the procedure of Examples 1 or 2 above with appropriate substitution of reactants. Compounds prepared are listed in Table IV below, with identification of process used, reagent, yield where determined and characterization of product obtained.

TABLE IV

Preparation and Properties of Pyrazolium Salts Represented by Formula (I)

| Compound | Method | Reagent | % Yield | Melting Point °C | Analysis Calculated | | Found |
|---|---|---|---|---|---|---|---|
| 4-Methoxy-1,2-dimethyl-3,5-diphenylpyrazolium bromide | A | $(CH_3)_2SO_4$, | 57 | 163 – 164 | C, | 60.18 | 59.83 |
|  |  |  |  |  | H, | 5.33 | 5.41 |
|  |  | aq. HBr |  |  | N, | 7.80 | 7.71 |
| 4-Methoxy-1,2-dimethyl-3,5-diphenylpyrazolium iodide | A | $(CH_3)_2SO_4$, | 78 | 167 – 168 | C, | 53.22 | 53.27 |
|  |  |  |  |  | H, | 4.71 | 4.85 |
|  |  | aq. HBr |  |  | N, | 6.90 | 6.93 |
| 4-Methoxy-1,2-dimethyl-3,5- | A | $(CH_3)_2SO_4$ | 74 | 104 – 105 | C, | 58.45 | 58.62 |

TABLE IV-continued

Preparation and Properties of Pyrazolium Salts Represented by Formula (I)

| Compound | Method | Reagent | % Yield | Melting Point °C | Analysis Calculated | | Found |
|---|---|---|---|---|---|---|---|
| diphenylpyrazolium methyl sulfate | | | | | H, | 5.68 | 5.77 |
| | | | | | N, | 7.17 | 7.22 |
| 4-Ethoxy-1,2-dimethyl-3,5-diphenylpyrazolium perchlorate | B | C$_2$H$_5$I/NaH/DMF | 29 | 91 – 93 | C, | 58.09 | 57.86 |
| | | | | | H, | 5.39 | 5.43 |
| | | | | | N, | 7.13 | 7.03 |
| 1,2-Dimethyl-3,5-diphenyl-4-n-propoxypyrazolium perchlorate | A | (CH$_3$)$_2$SO$_4$, aq. HClO$_4$ | 70 | 104 – 105 | C, | 59.03 | 58.96 |
| | | | | | H, | 5.07 | 5.76 |
| | | | | | N, | 6.89 | 6.79 |
| 4-Allyloxy-1,2-dimethyl-3,5-diphenylpyrazolium perchlorate | A | (CH$_3$)$_2$SO$_4$, aq. HClO$_4$ | 70 | 105 – 107 | C, | 59.30 | 59.24 |
| | | | | | H, | 5.22 | 5.24 |
| | | | | | N, | 6.92 | 6.82 |
| 1,2-Dimethyl-3,5-diphenyl-4-(2-propynyloxy)pyrazolium perchlorate | A | (CH$_3$)$_2$SO$_4$, aq. HClO$_4$ | — | 136 – 137 | C, | 59.63 | 59.61 |
| | | | | | H, | 4.75 | 4.84 |
| | | | | | N, | 6.95 | 6.75 |
| 1,2-Dimethyl-3,5-diphenyl-4-(2-propinyloxy)pyrazolium methyl sulfate | A | (CH$_3$)$_2$SO$_4$ Toluene | 26 | 154 – 155 | C, | 60.86 | 61.62 |
| | | | | | H, | 5.35 | 5.35 |
| | | | | | N, | 6.76 | 6.75 |
| | | | | | S, | 7.74 | 7.57 |
| 1-Ethyl-4-methoxy-2-methyl-3,5-diphenylpyrazolium perchlorate | A | (C$_2$H$_5$)$_2$SO$_4$, aq. HClO$_4$ | — | 148 – 149 | C, | 58.09 | 58.03 |
| | | | | | H, | 5.38 | 5.40 |
| | | | | | N, | 7.13 | 7.17 |
| 4-Methoxy-1-methyl-3,5-diphenyl-2-n-propyl-pyrazolium perchlorate, ½ H$_2$O | A | (n-C$_3$H$_7$)$_2$SO$_4$, aq. HClO$_4$ | 53 | 108.5 – 108.7 | C, | 57.76 | 57.96 |
| | | | | | H, | 5.82 | 5.74 |
| | | | | | N, | 6.74 | 6.30 |
| 1-Ethyl-4-methoxy-2-methyl-3,5-diphenylpyrazolium ethyl sulfate | A | (C$_2$H$_5$)$_2$SO$_4$ | 66 | — | C, | 60.27 | 58.65 |
| | | | | | H, | 6.26 | 6.35 |
| | | | | | N, | 6.69 | 6.48 |
| | | | | | S, | 7.66 | 7.40 |
| 4-Isobutoxy-1,2-dimethyl-3,5-diphenylpyrazolium methyl sulfate | A | (CH$_3$)$_2$SO$_4$ | 93 | 89 – 90 | C, | 61.10 | 61.55 |
| | | | | | H, | 6.53 | 6.68 |
| | | | | | N, | 6.48 | 6.57 |
| | | | | | S, | 7.40 | 7.70 |
| 4-Hexyloxy-1,2-dimethyl-3,5-diphenylpyrazolium methyl sulfate | A | (CH$_3$)$_2$SO$_4$ | 53 | 64 – 65 | C, | 62.59 | 62.11 |
| | | | | | H, | 7.00 | 6.77 |
| | | | | | N, | 6.08 | 5.70 |
| | | | | | S, | 6.95 | 6.41 |
| 4-Heptyloxy-1,2-dimethyl-3,5-diphenylpyrazolium methyl sulfate | A | (CH$_3$)$_2$SO$_4$ | 83 | — | C, | 63.27 | 63.21 |
| | | | | | H, | 7.22 | 7.42 |
| | | | | | N, | 5.90 | 5.42 |
| | | | | | S, | 6.72 | 6.43 |
| 1,2-Dimethyl-3,5-diphenyl-4-octyloxypyrazolium methyl sulfate | A | (CH$_3$)$_2$SO$_4$ | 39 | — | C, | 63.91 | 64.73 |
| | | | | | H, | 7.43 | 7.30 |
| | | | | | N, | 5.73 | 5.70 |
| | | | | | S, | 6.55 | 6.53 |
| 4-Decyloxy-1,2-dimethyl-3,5-diphenylpyrazolium methyl sulfate | A | (CH$_3$)$_2$SO$_4$ · H$_2$O | 58 | — | C, | 62.90 | 61.28 |
| | | | | | H, | 7.92 | 7.65 |
| | | | | | N, | 5.24 | 5.12 |
| | | | | | S, | 5.98 | 5.78 |
| 1,2-Dimethyl-3,5-diphenyl-4-tridecyloxypyrazolium methyl sulfate | A | (CH$_3$)$_2$SO$_4$ | 80 | — | C, | 66.64 | 66.22 |
| | | | | | H, | 8.30 | 8.41 |
| | | | | | N, | 5.01 | 5.09 |
| | | | | | S, | 5.73 | 5.76 |
| 4-Hexadecyloxy-1,2-dimethyl-3,5-diphenylpyrazolium methyl sulfate | A | (CH$_3$)$_2$SO$_4$ | 71 | — | C, | 67.97 | 67.21 |
| | | | | | H, | 8.72 | 8.76 |
| | | | | | N, | 4.66 | 4.19 |
| | | | | | S, | 5.37 | 5.06 |
| 4-[(Cyclohexylmethyl)oxy]-1,2-dimethyl-3,5-diphenyl-pyrazolium methyl sulfate | A | (CH$_3$)$_2$SO$_4$ | 43 | — | C, | 63.54 | 65.31 |
| | | | | | H, | 6.83 | 6.56 |
| | | | | | N, | 5.93 | 4.97 |
| | | | | | S, | 6.77 | 5.36 |
| 4-(2-Chloroallyloxy)-1,2-dimethyl-3,5-diphenyl-pyrazolium methyl sulfate | A | (CH$_3$)$_2$SO$_4$ | 36 | — | C, | 55.93 | 52.67 |
| | | | | | H, | 5.14 | 5.13 |
| | | | | | N, | 6.21 | 6.02 |
| | | | | | S, | 7.11 | 7.34 |
| | | | | | Cl, | 7.86 | 8.06 |
| 4-(5-Chloroallyloxy)-1,2-dimethyl-3,5-diphenyl-pyrazolium methyl sulfate | A | (CH$_3$)$_2$SO$_4$ | 86 | — | C, | 55.93 | 55.95 |
| | | | | | H, | 5.14 | 5.55 |
| | | | | | N, | 6.21 | 6.08 |
| | | | | | S, | 7.11 | 6.83 |
| | | | | | Cl, | 7.86 | 8.06 |
| 4-Propoxy-1,2-dimethyl-3,5-sulfate | A | (CH$_3$)$_2$SO$_4$ | 90 | — | C, | 58.16 | 58.16 |
| | | | | | H, | 6.47 | 6.20 |
| | | | | | N, | 6.42 | 6.29 |
| | | | | | S, | 7.35 | 7.62 |
| | | | | | (1 H$_2$O) | | |
| 4-Propoxy-1,2-dimethyl-3,5-diphenylpyrazolium chloride | A | (CH$_3$)$_2$SO$_4$, Dowex 1-X8 (Ionic Form Cl$^-$) | — | Hygroscopic solid | C, | 70.07 | 55.19 |
| | | | | | H, | 6.76 | 5.09 |
| | | | | | N, | 8.17 | 6.10 |
| | | | | | Cl, | 10.34 | 23.08 |
| 4-Propoxy-1,2-dimethyl-3,5-diphenylpyrazolium bromide | A | (CH$_3$)$_2$SO$_4$, HBr | — | — | C, | 62.02 | 61.45 |
| | | | | | H, | 5.99 | 6.28 |
| | | | | | N, | 7.24 | 7.14 |
| | | | | | Br, | 20.64 | 20.31 |
| 4-Propoxy-1,2-dimethyl-3,5-diphenylpyrazolium iodide | A | (CH$_3$)$_2$SO$_4$, KI | — | 140 – 141 | C, | 55.31 | 54.96 |
| | | | | | H, | 5.34 | 5.26 |
| | | | | | N, | 6.45 | 6.45 |
| | | | | | I, | 29.33 | 29.49 |

TABLE IV-continued

Preparation and Properties of Pyrazolium Salts Represented by Formula (I)

| Compound | Method | Reagent | % Yield | Melting Point ° C | Analysis Calculated | Found |
|---|---|---|---|---|---|---|
| 4-Isopropoxy-1,2-dimethyl-3,5-diphenylpyrazolium methyl sulfate | A | $(CH_3)_2SO_4$ | 95 | 95 – 98 | C, 57.78<br>H, 6.47<br>N, 6.42<br>S, 7.35<br>(1 $H_2O$) | 58.09<br>6.15<br>6.30<br>7.80 |
| 4-Isopropoxy-1,2-dimethyl-3,5-diphenylpyrazolium perchlorate | A | $(CH_3)_2SO_4$<br>$HClO_4$ | — | 145 – 147 | C, 59.03<br>H, 5.70<br>N, 6.89<br>Cl, 8.72 | 59.01<br>5.68<br>6.82<br>8.74 |
| 4-Butoxy-1,2-dimethyl-3,5-diphenylpyrazolium methyl sulfate | A | $(CH_3)_2SO_4$ | 73 | — | C, 61.10<br>H, 6.53<br>N, 6.48<br>S, 7.45 | 60.96<br>6.48<br>6.38<br>7.21 |
| 4-Butoxy-1,2-dimethyl-3,5-diphenylpyrazolium perchlorate | A | $(CH_3)_2SO_4$,<br>$HCLO_4$ | — | 124 – 125 | C, 59.94<br>H, 5.99<br>N, 6.82<br>Cl, 8.42 | 60.28<br>5.93<br>6.73<br>8.38 |
| 4-sec-Butoxy-1,2-dimethyl-3,5-diphenylpyrazolium methyl sulfate | A | $(CH_3)_2SO_4$ | 81 | 109 – 110 | C, 61.10<br>H, 6.53<br>N, 6.48<br>S, 7.41 | 61.58<br>6.55<br>6.35<br>7.33 |
| 4-sec-Butoxy-1,2-dimethyl-3,5-diphenylpyrazolium perchlorate | A | $(CH_3)_2SO_4$<br>$HClO_4$ | — | 149 – 150 | C, 59.94<br>H, 5.99<br>N, 6.66<br>Cl, 8.43 | 59.95<br>5.93<br>6.65<br>8.51 |
| 4-Pentoxy-1,2-dimethyl-3,5-diphenylpyrazolium methyl sulfate | A | $(CH_3)_2SO_4$ | 66 | — | C, 60.63<br>H, 6.86<br>N, 6.15<br>S, 7.04<br>(½ $H_2O$) | 60.76<br>6.89<br>5.99<br>6.97 |
| 4-Pentoxy-1,2-dimethyl-3,5-diphenylpyrazolium perchlorate | A | $(CH_3)_2SO_4$,<br>$HClO_4$ | — | 86 – 87 | C, 60.75<br>H, 6.26<br>N, 6.44<br>Cl, 8.15 | 60.46<br>6.18<br>6.25<br>8.12 |
| 4-(o-Chlorobenzyloxy)-1,2-dimethyl-3,5-diphenyl-pyrazolium methyl sulfate | A | $(CH_3)_2SO_4$ | 62.6 | 95 – 98 | C, 59.94<br>H, 5.03<br>N, 5.59<br>S, 6.40<br>Cl, 7.08 | 59.84<br>4.96<br>5.71<br>6.32<br>8.68 |
| 4-(m-Chlorobenzyloxy)-1,2-dimethyl-3,5-diphenyl-pyrazolium methyl sulfate | A | $(CH_3)_2SO_4$ | 90.7 | 77 – 79 | C, 59.94<br>H, 5.03<br>N, 5.59<br>S, 6.40<br>Cl, 7.08 | 59.62<br>4.94<br>5.69<br>6.18<br>7.05 |
| 4-(p-Chlorobenzyloxy)-1,2-dimethyl-3,5-diphenyl-pyrazolium methyl sulfate | A | $(CH_3)_2SO_4$ | 78.3 | — | C, 57.85<br>H, 5.25<br>N, 5.28<br>S, 6.18<br>Cl, 6.83<br>(1 $H_2O$) | 56.93<br>4.98<br>5.21<br>6.02<br>13.37<br>trace of $CHCl_3$ |
| 4-(p-Chlorobenzyloxy)-1,2-dimethyl-3,5-diphenyl-pyrazolium perchlorate | A | $(CH_3)_2SO_4$,<br>$HClO_4$ | — | 128 – 130 | C, 58.90<br>H, 4.53<br>N, 5.73<br>Cl, 14.49 | 59.53<br>4.65<br>5.73<br>14.78 |
| 4-(p-Methylbenzyloxy)-1,2-dimethyl-3,5-diphenyl-pyrazolium methyl sulfate | A | $(CH_3)_2SO_4$ | 70.7 | 105 – 108 | C, 64.99<br>H, 5.87<br>N, 5.83<br>S, 6.67 | 63.92<br>6.06<br>5.83<br>6.77 |
| 4-(p-Bromobenzyloxy)-1,2-dimethyl-3,5-diphenyl-pyrazolium methyl sulfate | A | $(CH_3)_2SO_4$ | 89.9 | 73 – 79 | C, 54.64<br>H, 4.59<br>N, 5.10<br>S, 5.83<br>Br, 14.54 | 52.72<br>4.73<br>4.95<br>6.27<br>13.20 |
| 4-(p-Bromobenzyloxy)-1,2-dimethyl-3,5-diphenyl-pyrazolium perchlorate | A | $(CH_3)_2SO_4$,<br>$HClO_4$ | — | 156 – 158 | C, 54.01<br>H, 4.16<br>N, 5.25<br>Br, 14.97<br>Cl, 6.64 | 53.79<br>4.08<br>5.13<br>15.11<br>6.43 |
| 4-(p-Methoxybenzyloxy-1,2-dimethyl-3,5-diphenyl-pyrazolium methyl sulfate | A | $(CH_3)_2SO_4$ | 78.4 | 105 – 107 | C, 62.87<br>H, 5.68<br>N, 5.64<br>S, 6.46 | 61.90<br>5.68<br>5.57<br>6.56 |
| 1,2-Dimethyl-3,5-diphenyl-4- [m-(trifluoromethyl)-benzyl]oxy pyrazolium methyl sulfate | A | $(CH_3)_2SO_4$ | 80 | — | C, 58.43<br>H, 4.72<br>N, 5.24<br>S, 6.00<br>F, 10.66 | 57.57<br>4.59<br>4.94<br>5.83<br>10.83 |
| 1,2-Dimethyl-3,5-diphenyl-4- [m-(trifluoromethyl)-benzyl]oxy pyrazolium perchlorate | A | $(CH_3)_2SO_4$,<br>$HClO_4$ | — | 157 – 158 | C, 57.42<br>H, 4.24<br>N, 5.36<br>Cl, 6.78<br>F, 10.90 | 56.99<br>4.31<br>5.16<br>7.08<br>10.52 |
| 4-(m-Cyanobenzyloxy)-1,2-dimethyl-3,5-diphenyl-pyrazolium methyl sulfate | A | $(CH_3)_2SO_4$ | 85.9 | — | C, 61.27<br>H, 5.34<br>N, 8.25<br>S, 6.29 | 61.60<br>4.95<br>8.05<br>6.10 |

TABLE IV-continued

Preparation and Properties of Pyrazolium Salts Represented by Formula (I)

| Compound | Method | Reagent | % Yield | Melting Point ° C | Analysis Calculated | Found |
|---|---|---|---|---|---|---|
| 4-(m-Cyanobenzyloxy)-1,2-dimethyl-3,5-diphenyl-pyrazolium perchlorate | A | (CH$_3$)$_2$SO$_4$<br>HClO$_4$ | — | 114 – 115 | (1 H$_2$O)<br>C, 62.57<br>H, 4.62<br>N, 8.76<br>Cl, 7.39 | 62.57<br>4.68<br>8.60<br>7.39 |
| 4-(p-Nitrobenzyloxy)-1,2-dimethyl-3,5-diphenyl-pyrazolium methyl sulfate | A | (CH$_3$)$_2$SO$_4$ | 81 | 128 – 129 | C, 58.71<br>H, 4.93<br>N, 8.22<br>S, 6.27 | 58.62<br>5.05<br>8.17<br>6.40 |
| 1,2-Dimethyl-4-(α-methyl-benzyloxy)-3,5-diphenyl-pyrazolium methyl sulfate | A | (CH$_3$)$_2$SO$_4$ | — | Hygroscopic solid | C, 60.40<br>H, 6.24<br>N, 5.42<br>S, 6.21 | 60.04<br>6.19<br>5.30<br>5.93 |
| 1,2-Dimethyl-4-(α-methyl-benzyloxy)-3,5-diphenyl-pyrazolium perchlorate | A | (CH$_3$)$_2$SO$_4$<br>HClO$_4$ | — | 166 – 167 | (2 H$_2$O)<br>C, 64.05<br>H, 5.38<br>N, 5.98<br>Cl, 7.56 | 63.87<br>5.17<br>5.69<br>6.87 |
| 1,2-Dimethyl-4-(p-nitro-phenoxy)-3,5-diphenyl-pyrazolium methyl sulfate | A | (CH$_3$)$_2$SO$_4$ | 71 | 178 – 179 | C, 55.89<br>H, 4.89<br>N, 8.15<br>S, 6.22 | 55.62<br>4.07<br>7.86<br>6.15 |
| 1,2-Dimethyl-4-(p-chloro-phenoxy)-3,5-diphenyl-pyrazolium methyl sulfate | A | (CH$_3$)$_2$SO$_4$ | 96.5 | 133 – 138 | (1 H$_2$O)<br>N, 5.75<br>S, 6.59 | 5.05<br>5.89 |
| 1,2-Dimethyl-4-phenoxy-3,5-diphenylpyrazolium methyl sulfate | A | (CH$_3$)$_2$SO$_4$ | 27.3 | Hygroscopic solid | | |
| 4-Benzyloxy-1,2-dimethyl-3,5-diphenylpyrazolium methyl sulfate | A | DMS<br>Xylene | 78 | 131 – 132 | C, 63.42<br>H, 5.77<br>N, 6.16 | 64.23<br>5.68<br>5.93 |
| 4-Benzyloxy-1,2-dimethyl-3,5-diphenylpyrazolium perchlorate | A | DMS<br>aq. HClO$_4$ | — | 198 – 199 | C, 63.37<br>H, 5.10<br>N, 6.16 | 63.52<br>5.26<br>6.07 |
| 4-Benzyloxy-1,2-dimethyl-3,5-diphenylpyrazolium tetrafluoroborate | A | DMS<br>aq. NaBF$_4$ | — | 178 – 179.5 | C, 65.18<br>H, 5.24<br>N, 6.33 | 65.28<br>5.30<br>6.37 |
| 4-Benzyloxy-3,5-diphenyl-1,2-diethylpyrazolium ethyl sulfate | A | Methyl Sulfate (DES)<br>Benzene | 31 | oil | C, 63.86<br>H, 6.50<br>N, 5.32<br>S, 6.09 | 62.60<br>6.18<br>5.50<br>6.36 |
| 4-Benzyloxy-3,5-diphenyl-1-ethyl-2-methylpyrazolium iodide | A | DMS<br>Benzene | 45 | 148.5 – 150.0 | (H$_2$O)<br>C, 60.49<br>H, 5.08<br>N, 5.64<br>I, 25.57 | 60.45<br>4.90<br>5.58<br>25.55 |
| 4-Benzyloxy-3,5-diphenyl-2-methyl-1-n-propyl-pyrazolium iodide | A | DMS<br>aq. NaI | — | 106 – 138 (oil) | C, 61.18<br>H, 5.33<br>M, 5.49<br>O, 24.86 | |
| 4-Benzyloxy-3,5-diphenyl-1-2-methyl-1-n-propyl-methyl sulfate | A | DMS<br>Benzene | 65 | oil | C, 65.57<br>H, 6.11<br>N, 5.67<br>S, 6.48 | 65.40<br>6.05<br>5.72<br>6.44 |
| 1-Benzyl,3,5-diphenyl-4-methoxy-2-methylpyrazolium methyl sulfate, H$_2$O | A | (CH$_3$)$_2$SO$_4$ | — | oil | C, 61.98<br>H, 5.83<br>N, 5.78 | 61.92<br>5.99<br>5.48 |
| 1-Benzyl-3,5-diphenyl-4-methoxy-2-methylpyrazolium perchlorate | A | (CH$_3$)$_2$SO$_4$,<br>HClO$_4$ | 28 | 165 – 166.5 | C, 63.36<br>H, 5.10<br>N, 6.16 | 61.87<br>5.05<br>6.03 |
| 3,5-Diphenyl-1-methyl-4-methoxy-2-propylpyrazolium perchlorate | A | Dipropyl Sulfate<br>HClO$_4$ | 49 | 108.5 – 108.7 | C, 59.04<br>H, 5.70<br>N, 6.89 | 57.96<br>5.74<br>6.30 |
| 5-(p-Chlorophenyl)-1,2-dimethyl-3-phenyl-4-propoxypyrazolium methyl sulfate | A | (CH$_3$)$_2$SO$_4$ | 86 | 64 – 65 | C, 55.68<br>H, 5.56<br>N, 6.19<br>S, 7.08<br>Cl, 7.83 | 55.39<br>5.89<br>6.05<br>7.08<br>7.76 |
| 5-(p-Chlorophenyl)-1,2-dimethyl-3-phenyl-4-propoxypyrazolium perchlorate | A | (CH$_3$)$_2$SO$_4$<br>HClO$_4$ | — | 147 – 148 | C, 54.44<br>H, 5.03<br>N, 6.35<br>Cl, 16.08 | 54.87<br>5.10<br>6.28<br>16.03 |
| 1,2-Dimethyl-4-propoxy-3,5-di-p-tolylpyrazolium tetrafluoroborate | A | (CH$_3$)$_2$SO$_4$,<br>aq. NaBF$_4$ | — | 124.5 – 126.5 | C, 62.58<br>H, 6.45<br>N, 6.63<br>F, 17.99 | 62.49<br>6.67<br>6.59<br>17.82 |
| 1,2-Dimethyl-3-phenyl-4-propoxy-5-m-tolylpyrazolium methyl sulfate | A | (CH$_3$)$_2$SO$_4$ | 67 | 73 – 79 | C, 61.09<br>H, 6.52<br>N, 6.48<br>S, 7.41 | 61.34<br>6.48<br>6.44<br>7.60 |
| 3,5-bis(m-Chlorophenyl)-1,2-dimethyl-4-propoxy-pyrazolium methyl sulfate | A | (CH$_3$)$_2$SO$_4$ | 69 | 151.5 – 153.7 | C, 51.75<br>H, 4.96<br>N, 5.75<br>S, 6.56<br>Cl, 14.55 | 51.65<br>4.64<br>5.64<br>6.69<br>14.83 |
| 1,2-Dimethyl-3-phenyl-4-propoxy-5-p-tolylpyrazolium | A | (CH$_3$)$_2$SO$_4$ | 96 | Yellow Gum | C, 59.85<br>H, 6.62 | 60.15<br>6.42 |

TABLE IV-continued
Preparation and Properties of Pyrazolium Salts Represented by Formula (I)

| Compound | Method | Reagent | % Yield | Melting Point ° C | Analysis | |
|---|---|---|---|---|---|---|
| | | | | | Calculated | Found |
| methyl sulfate . ½H₂O | | | | | N, 6.34 | 6.17 |
| | | | | | S, 7.26 | 7.13 |
| 1,2-Dimethyl-4-propoxy-3,5-di-m-tolylpyrazolium methyl sulfate | A | (CH₃)₂SO₄ | 79 | 91 – 93 | C, 61.86 | 62.01 |
| | | | | | H, 6.77 | 6.78 |
| | | | | | N, 6.27 | 6.26 |
| | | | | | S, 7.18 | 7.24 |
| 3-o-Chlorophenyl-1,2-dimethyl-5-phenyl-4-propoxypyrazolium methyl sulfate, hydrated | A | (CH₃)₂SO₄ | 85 | Glass | C, 55.68 | 55.33 |
| | | | | | H, 5.56 | 5.55 |
| | | | | | N, 6.18 | 5.91 |
| | | | | | S, 7.08 | 6.72 |
| 3-(p-Chlorophenyl)-4-methoxy-1,2-dimethyl-5-phenyl-pyrazolium methyl sulfate | A | (CH₃)₂SO₄ | 66.4 | 110 – 111 | C, 53.70 | 55.89 |
| | | | | | H, 4.98 | 5.43 |
| | | | | | N, 6.60 | 6.03 |
| | | | | | S, 7.55 | 7.16 |
| | | | | | Cl, 8.34 | 7.86 |
| 3-(p-Chlorophenyl)-4-methoxy-1,2-dimethyl-5-phenyl-pyrazolium perchlorate | A | (CH₃)₂SO₄ HClO₄ | — | 76 – 78 | C, 52.30 | 52.53 |
| | | | | | H, 4.39 | 4.47 |
| | | | | | N, 6.78 | 6.67 |
| | | | | | Cl, 17.16 | 17.15 |

Additional exemplary matter is presented hereinbelow to illustrate and/or describe the preparation of the useful and novel pyrazoles, represented by the structure (II):

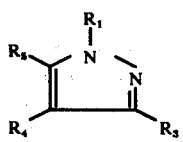

wherein $R_1$ represents a member selected from the group consisting of hydrogen, alkyl $C_1$–$C_3$ and benzyl; $R_3$ is

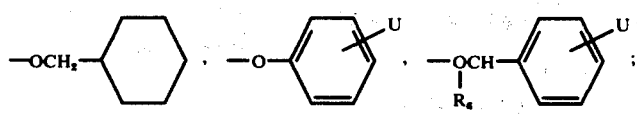

$R_4$ represents a member selected from the group consisting of alkoxy $C_1$–$C_{16}$, alkenyloxy $C_3$–$C_4$, halogen substituted alkenyloxy $C_3$–$C_4$, alkynyloxy $C_3$–$C_4$,

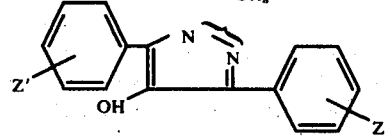

$R_6$ represents a member selected from the group consisting of hydrogen and methyl; U represents a member selected from the group consisting of hydrogen, halogen, methyl, methoxy, $NO_2$, 2,4-di-$NO_2$, CN and $CF_3$; and Z and Z' each represent a member selected from the group consisting of hydrogen, halogen and methyl; the proviso that when $R_1$ is ethyl, $R_4$ cannot be ethoxy; n is an integer from 1, 2, 3 or 4; said formula (II) pyrazoles being essential intermediates in the preparation of the novel formula (I) pyrazolium fungicides of the present invention.

Non-limiting examples are also given hereinbelow for the preparation of pyrazoles of the structure (IV):

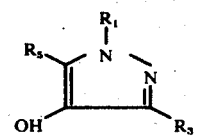

wherein $R_1$, $R_3$ and $R_5$ are as above-described, and said formula IV pyrazoles are intermediates useful in the preparation of the formula II pyrazoles described above.

EXAMPLE 7

This example illustrates a method for the preparation of
4-hydroxy-1-methyl-3,5-di(substituted-phenyl)-pyrazoles The procedure of M. J. Nye and W. P. Tang, Can. J. Chem. 51: 338 (1973), is followed. A mixture of 2-acetoxy-1,3-di(substituted-phenyl)-1,3-propanedione and methylhydrazine are allowed to react in n-propanol. Upon isolation of the product as described, the subject compounds are obtained. The compounds are listed in Table II below:

TABLE V

| Z | Z' | Melting Point ° C |
|---|---|---|
| 2-chloro | H | |
| 4-chloro | H | 179–181 |
| 3-chloro | 3-chloro | 128–132 |

TABLE V-continued

[Structure: pyrazole with CH₃ on N, OH on 4-position, Z and Z' substituents on phenyl rings]

| Z | Z' | Melting Point °C |
|---|---|---|
| 3-methyl | H | and 138.5<br>131–135 |
| 4-methyl | H | 168–170 |
| 3-methyl | 3-methyl | 143–145 |
| 4-methyl | 4-methyl | 182–184 |

EXAMPLE 8

Preparation of 1-Benzyl-3,5-diphenyl-4-pyrazolol, acetate (ester)

Sodium acetate (5.13 g, 0.626 mole) is added to a mixture of 2-hydroxy-1,3-diphenyl-1,3-propanedione, acetate (8 g, 0.0283 mole), benzyl hydrazine dihydrochloride (6.1 g, 0.0313 mole) and 1-propanol (80 ml). The reaction mixture is stirred and heated slowly to 80° C. After heating for 2 hours, the mixture is poured into water. The solid formed, 11 g (105%), is isolated by filtration and recrystallized from methanol to give a white crystalline solid, melting poing 103°–103.5° C.

Analyses calculated for $C_{24}H_{20}N_2O_2$: C, 78.24; H, 5.47; N, 7.60. Found: C, 78.45; H, 5.66; N, 7.73.

EXAMPLE 9

Preparation of 1-Benzyl-3,5-diphenyl-4-pyrazolol.

A solution of sodium hydroxide (1.5 g, 0.0375 mole), methanol (30 ml) and water (30 ml) is added to 1-benzyl-3,5-diphenyl-4-pyrazolol, acetate (6.9 g, 0.019 mole) and the mixture stirred and refluxed for one hour. A white solid forms and is isolated by filtration, treated with dilute hydrochloric acid, washed with water and dried to give a white solid, 6.36 g, melting point 194°–195° C.

Analyses calculated for $C_{22}H_{18}N_2O$: C, 80.95; H, 5.56; N, 8.58. Found: C, 80.87; H, 5.67; N, 8.53.

EXAMPLE 10

General Methods for Preparation of 4-Alkoxy-1-methyl-3,5-diphenylpyrazoles and 3,5-di(substituted-phenyl)pyrazoles. Method A A mixture of 1-methyl-3,5-diphenyl-4-pyrazolol (0.04 mole) (or the appropriate substituted-phenyl pyrazole), benzyltriethylammonium chloride (1 g), the appropriate alkyl halide (0.08 mole) and aqueous sodium hydroxide (0.08 mole in 46 ml water) is stirred vigorously and heated at 60°–70° C for 24 hours. The reaction is followed by glc.

The cooled reaction mixture is extracted with methylene chloride. The methylene chloride layer is separated, washed with 10% aqueous sodium hydroxide solution, then washed well with water, dried (Drierite) and stripped in vacuo.

Method B

A mixture of 1-methyl-3,5-diphenyl-4-pyrazolol (0.06 mole), sodium methoxide (0.06 mole) and methanol (200 ml) is stirred and refluxed for 2 hours. The reaction mixture is then evaporated to dryness and azeotropically dried with toluene. The toluene is removed in vacuo and the residue dissolved in dry DMF (250 ml). The appropriate alkyl ester of p-toluenesulfonic acid (0.06 mole) is added, and the reaction mixture stirred overnight at room temperature. The reaction is followed by glc. The reaction mixture is heated at 50°–75° C as required to complete the reaction.

The cooled reaction mixture is poured into water and extracted with ether. The ether layer is separated, washed with 10% aqueous sodium hydroxide solution, washed well with water and then stripped in vacuo.

Method C

A mixture of 1-methyl-3,5-diphenyl-4-pyrazolol (0.02 mole), DMF (50 ml) and potassium t-butoxide or sodium methoxide (0.02 mole) is stirred and heated at 50° C for one hour. The appropriate aliphatic halide (0.04 mole) is added and the mixture heated at 55°–60° C for 2 to 3 hours.

The reaction mixture is poured into water and made alkaline with 1% aqueous sodium hydroxide solution. Crude solid products are isolated by filtration. In the case of oils, the products are isolated by extraction with chloroform. The chloroform layer is separated, washed with water and stripped in vacuo.

Compounds prepared by these methods are listed in Tables V and VI.

TABLE V

[Structure: 1-methyl-3,5-diphenylpyrazole with OR₄ at 4-position]

| R₄ | Melting Point °C | Method | Recrystallizing Solvent |
|---|---|---|---|
| CH₃ | 88–89 | (CH₃O)₂SO₂ + NaOH | — |
| (CH₃)₂CH— | 114–118 | A | Hexane |
| (CH₃)₂CHCH₂— | 60–61 | A | Hexane |
| C₂H₅CH(CH₃)— | 93–94 | A | Methanol |
| CH₃(CH₂)₄— | 68 | A | Hexane |
| CH₃(CH₂)₅— | oil | A | Chromatographed on silica gel with benzene, followed by recrystallization from hexane |
| CH₃(CH₂)₆— | oil | A | Chromatographed, silica gel, toluene |
| CH₃(CH₂)₇— | oil | A | Chromatographed, silica gel, toluene |
| (CH₃(CH₂)₉— | oil | B | Chromatographed, silica gel, toluene |
| CH₃(CH₂)₁₂— | oil | B | Silica gel, toluene |
| CH₃(CH₂)₁₅— | oil | B | Silica gel, toluene |
| ⌬—CH₂— | 95–97 | A | Hexane |
| CH₂=CHCH₂— | 58–59 | C | Hexane |

TABLE V-continued

[Structure: 1-methyl-3,5-diphenylpyrazole with OR₄ at 4-position]

| R₄ | Melting Point °C | Method | Recrystallizing Solvent |
|---|---|---|---|
| CH≡CCH₂— | 74.5–75 | C | Chromatographed, silica gel, benzene, recrystallization from methanol |
| CH₂=CClCH₂— | 58–59 | C | Silica gel, toluene |
| ClCH=CHCH₂— | oil | C | Silica gel, toluene |

TABLE VI

[Structure: 1-methyl-3,5-bis(substituted phenyl)pyrazole with OR₄ at 4-position, Z' on one ring, Z on other]

| Z | R₄ | Z' | Melting Point °C | Method |
|---|---|---|---|---|
| 2-chloro | n-propyl | H | oil | A |
| 4-chloro | n-propyl | H | 84–86 | A |
| 3-chloro | n-propyl | 3-chloro | oil | A |
| 3-methyl | n-propyl | H | oil | A |
| 4-methyl | n-propyl | H | oil | A |
| 3-methyl | n-propyl | 3-methyl | oil | A |
| 4-methyl | n-propyl | 4-methyl | 78.5–80 | A |

EXAMPLE 11

General Method for Preparation of 4-Benzyloxy-1-methyl-3,5-diphenylpyrazoles

A mixture of 4-hydroxy-1-methyl-3,5-diphenylpyrazole (0.04 mole), sodium methoxide (0.045 mole) and dry DMF (100 ml) is stirred and heated to 60° C. The reaction mixture is cooled to room temperature and the substituted-benzyl halide (chloride or bromide) (0.05 mole) added dropwise. If the substituted-benzyl halide is a solid, a solution is prepared using dry DMF (50 ml). Stirring is continued and the reaction mixture heated at 55°–60° C until the reaction is complete. The reaction is followed by tlc (CHCl₃/silica gel). The mixture is then cooled and poured into an excess of water. The aqueous mixture is made alkaline by the addition of 1N sodium hydroxide and extracted with ether. The ether layer is separated, washed well with water, dried and stripped in vacuo.

The compounds prepared by this method are listed in Table VII.

tripped in vacuo to give a clear yellow oil, which upon standing became a solid. The crude product is slurried with pentane. The product is isolated by filtration and obtained as a white crystalline solid, 2 g (24%), melting point 100°–103° C.

TABLE VII

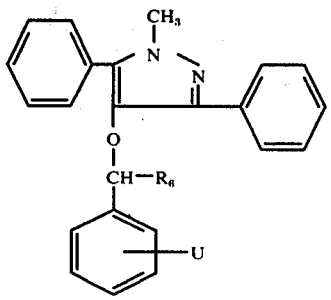

| U | $R_6$ | Melting Point °C | Recrystallizing Solvent |
|---|---|---|---|
| H | H | 128–129.5 | Acetonitrile |
| 2-chloro | H | 64–69 | Eluted on silica gel with $CHCl_3$ |
| 3-chloro | H | 85–86 | Eluted on silica gel with $CHCl_3$, followed by recrystallization from methylcyclohexane |
| 4-chloro | H | oil | Eluted on silica gel with $CHCl_3$ |
| 4-bromo | H | oil | Eluted on silica gel with $CHCl_3$ |
| 2,6-dichloro | H | 110–118 | Methylcyclohexane, followed by Eluting on silica gel with $CHCl_3$ |
| 3,4-dichloro | H | 102–104 | Eluted on silica gel with $CHCl_3$ |
| 4-methoxy | H | 71–72 | Eluted on silica gel with benzene, followed by recrystallization from methylcyclohexane |
| 3-trifluoromethyl | H | 84–85 | Hexane |
| 3-cyano | H | 90–92 | Acetonitrile |
| 4-Nitro | H | 84–85 | Eluted on silica gel with $CHCl_3$, followed by recrystallization from methanol |
| H | Methyl | 132–133 | Methanol |

EXAMPLE 12

Preparation of 3-(p-Chlorophenyl)-4-methoxy-1-methyl-5-phenyl [and 5-(p-Chlorophenyl)-4-methoxy-1-methyl-3-phenyl]-pyrazole.

A mixture of 3-(p-chlorophenyl)-1-methyl-5-phenyl [and 5-(p-chlorophenyl)-1-methyl-3-phenyl]-4-pyrazolol (7.9 g, 0.0278 mole) and 20% aqueous sodium hydroxide solution (200 ml) is stirred and heated to 60° C. Dimethyl sulfate (20.7 ml, 0.222 mole) is added to the turbid yellow solution. An exotherm is observed and the temperature of the reaction mixture rose to 80° C. Stirring is continued and the mixture is allowed to cool to room temperature. A buff-colored gum is formed. The aqueous layer is decanted away from the gum and the gum washed well with water until neutral. The yellow gum, 5.5 g, is dissolved in ether and filtered through a bed of neutral alumina. The filtrate is Analyses calculated for $C_{17}H_{15}N_2OCl$: C, 68.33; H, 5.06; N, 9.38; Cl, 11.86. Found: C, 68.18; H, 4.89; N, 9.39; Cl, 12.10.

EXAMPLE 13

General Method for the Preparation of 1-Substituted-4-benzyloxy-3,5-diphenylpyrazoles A mixture of 4-benzyloxy-3,5-diphenylpyrazole (0.0278 mole), potassium t-butoxide (0.0306 mole) and 2-propanol (90 ml) is stirred well at room temperature until a clear solution forms. The appropriate alkyl (or arylalkyl) halide (0.0337 mole) is added dropwise. The reaction mixture is stirred for one to two days at room temperature and then is heated at 50° C for 2 to 4 hours. The mixture is poured into water and extracted with chloroform or toluene. The chloroform or toluene layer is separated, washed well with water, dried and stripped in vacuo to give an oil or a solid.

The compounds prepared by this method are listed in Table VIII below.

Table VIII

1-Substituted-4-benzyoxy-3,5-diphenylpyrazole

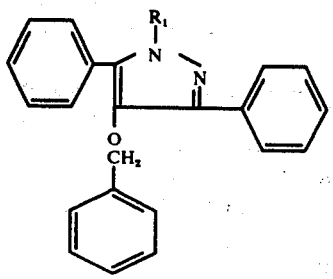

| R₁ | Alkylating Agent | Method of Purification | Melting Point °C |
|---|---|---|---|
| C₂H₅ | C₂H₅I | Eluted on silica gel with chloroform followed by recrystallization from 2-propanol | 54–55 |
| n-C₃H₇ | n-C₃H₇Br | Recrystallized from acetonitrile | 69–70 |
| ⌬-CH₂ | ⌬-CH₂Cl | Recrystallized from 2-propanol | 64.5–68.5 |

EXAMPLE 14

Preparation of 4-(n-Propoxy)-3,5-diphenylpyrazole

A mixture of 3,5-diphenyl-4-pyrazolol (10 g, 0.042 mole), sodium methoxide (2.27 g, 0.042 mole) and methanol (60 ml) is heated at 60° C for 2 hours. Then 1-bromopropane (5.17 g, 0.042 mole) is added slowly (5 minutes) at 60° C. The reaction mixture is then held at 60° C until the reaction is complete by tlc. The mixture is poured into water and the solid formed is isolated by filtration. Recrystallization of the solid from acetonitrile affords white crystals, 7.4 g (63%), melting point 142°–142.5° C.

Analyses calculated for $C_{18}H_{18}N_2O$: C, 77.67; H, 6.52; N, 10.07. Found: C, 77.46; H, 6.60; N, 9.97.

EXAMPLE 15

Preparation of 4-(Benzyloxy)-3,5-diphenylpyrazole

A mixture of 3,5-diphenyl-4-pyrazolol (10 g, 0.042 mole), sodium methoxide (2.27 g, 0.042 mole) and methanol (60 ml) is heated at 60° C for 2 hours. Then benzyl chloride is added slowly at 60° C. A white solid forms. Heating is continued overnight at 60° C. The reaction mixture is examined by glc and the reaction is found to be complete. The mixture is poured into water and the solid isolated by filtration. The solid is washed well with water, dried and recrystallized from acetonitrile to give pale yellow crystals, melting point 152°–152.5° C.

Analyses calculated for $C_{22}H_{18}N_2O$: C, 80.95; H, 5.56; N, 8.58. Found: C, 80.77; H, 5.71; N, 8.69.

EXAMPLE 16

Preparation of 1-Methyl-3,5-diphenyl-4-n-propoxypyrazole

Sodium hydride (57%, 0.92 g, 0.022 mole) is added slowly to a suspension of 1-methyl-3,5-diphenyl-4-pyrazolol (5 g, 0.02 mole) in anhydrous ether (100 ml). An off-white precipitate forms. After stirring for 45 minutes, the solid is removed by filtration, added to dry DMF (30 ml) and treated with 1-iodopropane (5 ml. 0.05 mole). The reaction mixture is stirred, heated at 60° C for 14 hours and then poured into ice water (600 ml). After standing for 24 hours in the refrigerator, a tacky yellow solid is formed. Recrystallization from hexane at −20° C affords an off-white solid, melting point 56°–57° C.

Analyses calculated for $C_{19}H_{20}N_2O$: C, 78.05; H, 6.90; N, 9.58. Found: C, 78.04; H, 6.90; H, 9.49.

EXAMPLE 17

Preparation of 4-n-Butoxy-1-methyl-3,5-diphenylpyrazole

A mixture of 1-methyl-3,5-diphenyl-4-pyrazolol (25 g, 0.1 mole), sodium hydroxide (56 g, 1.4 mole) and water (800 ml) is stirred until all the sodium hydroxide dissolved. The reaction mixture was heated, filtered and the filtrate stirred vigorously, and 1-iodobutane (22.8 ml, 0.2 mole) added dropwise. The reaction mixture is refluxed for 22 hours. Acetonitrile (700 ml) is added to the reaction mixture to give a homogeneous solution and more 1-iodobutane (10 ml, 0.09 mole) added. After refluxing for 3 hours, the reaction mixture is cooled, extracted with ether and the ether layer separated. The ether layer is washed well with water, dried and stripped in vacuo to give a viscous orange oil, 24.35 g.

The oil is dissolved in hexane (35 ml), filtered through neutral alumina and the filtrate stored overnight at 0° C. Pale yellow crystals formed and are isolated by filtration and dried to give a solid, 7.0 g (23%), melting point 48°–49.5° C.

Analyses calculated for $C_{20}H_{22}N_2O$: C, 78.40; H, 7.24; N, 9.14. Found: C, 78.61; H, 7.53; N, 9.25.

EXAMPLE 18

Preparation of 4-tert-Butoxy-1-methyl-3,5-diphenylpyrazole.

4-Bromo-1-methyl-3,5-diphenylpyrazole (31.3 g, 0.1 mole) and dry tetrahydrofuran (250 ml) are stirred under a nitrogen atmosphere and cooled to −30° C to −40° C. A solution of n-butyllithium (50 ml, 2.4 moles) is added and the deep red solution formed is stirred for ½ hours and allowed to warm to −20° C. The reaction mixture is cooled to −60° C, and a solution of tert-butylperoxybenzoate (19.4 g, 0.1 mole) and dry tetrahydrofuran (50 ml) added dropwise over a ½ hour period. During the addition, the reaction mixture became dark and then lighter in color. The mixture is stirred for ½ hour at −60° C and a solid is formed. The mixture is poured into 10% aqueous hydrochloric acid (400 ml) and the mixture stirred for 10 minutes. The upper organic layer is separated, washed consecutively with 10% aqueous hydrochloric acid (100 ml), with water, with 4% aqueous sodium hydroxide solution (2 × 200 ml) and finally with water. The organic layer is separated and treated with hexane (200 ml). A solid forms, and is removed by filtration.

Stripping of the mother liquor in vacuo affords an oil. The oil is chromatographed on silica gel with toluene. A major component is isolated and recrystallized from hexane to give 4-tert-butoxy-1-methyl-3,5-diphenylpyrazole, 1.0 g (3.4%), melting point 106°–107.5° C.

Analyses calculated for $C_{20}H_{22}N_2O$: C, 78.40; H, 7.34; N, 9.14. Found: C, 78.37; H, 7.22; N, 9.10.

EXAMPLE 19

Preparation of 1-Methyl-4-(p-nitrophenoxyl)-3,5-diphenylpyrazole

A solution of 4-hydroxy-1-methyl-3,5-diphenylpyrazole (10 g, 0.04 mole), potassium t-butoxide (4.5, 0.04 mole) and dry DMF (150 ml) is stirred and heated to 60° C. The green fluorescent solution is cooled to room temperature and p-chloronitrobenzene (6.0 g, 0.038 mole) is added. The dark green solution is heated at 60° C for 24 hours and then poured into water, made alkaline with 1N sodium hydroxide and extracted with ether. The ether layer is separated, washed well with water, dried and stripped in vacuo to give a bright yellow solid 12.9 g (86.5%), m.p. 85° C to 110° C. The solid is chromatographed on silica gel with benzene to give a yellow crystalline solid 11.3 g, m.p. 74° C to 100° C. Recrystallization from methanol (185 ml) affords white crystals 5.5 g (37%) m.p. 120° C to 122° C.

Analysis calculated for $C_{22}H_{17}N_3O_3$: C, 71.15; H, 4.61; N, 11.32. Found: C, 70.55; H, 4.65; N, 11.20.

A second crop 2.35 g (15.8%), m.p. 119° C to 120° C is obtained by chilling the mother liquor.

EXAMPLE 20

Preparation of 4-(p-Chlorophenoxy)-1-methyl-3,5-diphenylpyrazole

A solution of soldium nitrite (3.1 g, 0.0442 mole) in water (10 ml) is added slowly at 0° C to 5° C to a well stirred, chilled solution of 4-(p-aminophenoxy)-1-methyl-3,5-diphenylpyrazole (15.1 g, 0.0442 mole) in concentrated hydrochloric acid (50 ml).

This cold reaction mixture is added at 0° C to 5° C to a well stirred, chilled solution of cuprous chloride (4.85 g, 0.049 mole) in concentrated hydrochloric acid (50 ml). The reaction mixture is held at 0° C for half hour, then allowed to warm up to room temperature and finally heated on a steambath for half hour. The reaction mixture is cooled and the solid isolated by filtration.

The tan solid 16.1 g is chromatographed silica gel with chloroform to give a white solid 9.7 g (54.9%), m.p. 99° C to 102° C.

Analysis calculated for $C_{22}H_{17}ClN_2O$: c, 73.22; H, 4.75; N, 7.77; Cl, 9.83. Found C, 72.98; H, 4.61; N, 7.67 Cl, 9.78.

I claim:

1. A method for protecting living beneficial plants from fungi comprising applying to the foliage of said plants a fungicidally effective amount of a compound having the formula:

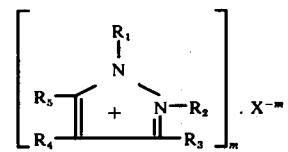

wherein $R_1$ and $R_2$ each represent $C_1$-$C_3$ alkyl or benzyl; $R_3$ and $R_5$ each represent a member selected from the group consisting of phenyl, halophenyl and tolyl; $R_4$ represents a member selected from the group consisting of $C_1$-$C_{16}$ alkoxy, $C_3$-$C_4$ alkenyloxy, $C_3$-$C_4$ alkynyloxy, $C_3$-$C_4$ haloalkenyloxy,

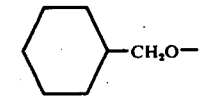

and

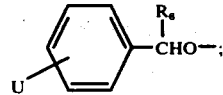

where $R_6$ represents hydrogen or methyl, U represents a member selected from the group consisting of hydrogen, methyl, methoxy, halogen, cyano, trifluoromethyl, nitro and 2,4-dinitro; X represents an anion with a charge of from 1 to 3; and m represents an integer from 1 to 3.

2. The method according to claim 1 wherein $R_1$ represents methyl or ethyl; $R_2$ is methyl; $R_3$ represents phenyl or m-chlorophenyl; $R_5$ is a member selected from the group consisting of phenyl, m-chlorophenyl and m-tolyl; $R_4$ represents a member selected from the group consisting of methoxy, ethoxy, propoxy, butoxy, pentyloxy, hexyloxy, heptyloxy, octyloxy, decyloxy, tridecyloxy, hexadecyloxy, allyloxy, 3-chloroallyloxy, 2-propynyloxy, benzyloxy, chloro- and bromobenzyloxy, trifluoromethylbenzyloxy, methylbenzyloxy, methoxybenzyloxy and

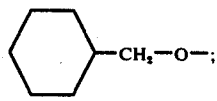

X represents an anion selected from the group consisting of bromide, chloride, iodide, methyl sulfate and perchlorate.

3. The method according to claim 1 wherein $R_1$ and $R_2$ each represent methyl; $R_3$ and $R_5$ each represent phenyl; $R_4$ represents a member selected from the group consisting of methoxy, propoxy, butoxy, pentyloxy, hexyloxy, heptyloxy, tridecyloxy, hexadecyloxy, allyloxy, 2-propynyloxy and benzyloxy; X represents an anion selected from the group consisting of bromide, chloride, methyl sulfate and perchlorate.

4. The method according to claim 1 wherein the compound is 1,2-dimethyl-3,5-diphenyl-4-methoxypyrazolium methyl sulfate.

5. The method according to claim 1 wherein the compound is 1,2-dimethyl-3,5-diphenyl-4-ethoxypyrazolium perchlorate.

6. The method according to claim 1 wherein the compound is 1,2-dimethyl-3,5-diphenyl-4-n-propoxypyrazolium methyl sulfate.

7. The method according to claim 1 wherein the compound is 4-n-butoxy-1,2-dimethyl-3,5-diphenylpyrazolium methyl sulfate.

8. The method according to claim 1 wherein the compound is 4-iso-butoxy-1,2-dimethyl-3,5-diphenylpyrazolium methyl sulfate.

9. The method according to claim 1 wherein the compound is 1,2-dimethyl-3,5-diphenyl-4-n-pentyloxypyrazolium methyl sulfate.

10. The method according to claim 1 wherein the compound is 1,2-dimethyl-3,5-diphenyl-4-n-hexyloxypyrazolium methyl sulfate.

11. The method according to claim 1 wherein the compound is 1,2-dimethyl-3,5-diphenyl-4-n-heptyloxypyrazolium methyl sulfate.

12. The method according to claim 1 wherein the compound is 1,2-dimethyl-3,5-diphenyl-4-n-tridecyloxypyrazolium methyl sulfate.

13. The method according to claim 1 wherein the compound is 1,2-dimethyl-3,5-diphenyl-4-n-hexadecyloxypyrazolium methyl sulfate.

14. The method according to claim 1 wherein the compound is 4-allyloxy-1,2-dimethyl-3,5-diphenylpyrazolium methyl sulfate.

15. The method according to claim 1 wherein the compound is 1,2-dimethyl-3,5-diphenyl-4-(2-propynyloxy)pyrazolium methyl sulfate.

16. The method according to claim 1 wherein the compound is 4-benzyloxy-1,2-dimethyl-3,5-diphenylpyrazolium methyl sulfate.

17. The method according to claim 1 wherein said compound is applied to the foliage of plants in the form of a liquid spray containing 50 ppm to 5600 ppm of said compound.

18. The method according to claim 1 wherein the plants to be protected are selected from the group consisting of cereal grains, fruit trees, nut trees, ornamentals, shrubs and fruit bearing vines.

* * * * *